(12) United States Patent
Li

(10) Patent No.: US 10,246,571 B2
(45) Date of Patent: *Apr. 2, 2019

(54) POLYFUNCTIONAL AMINES WITH HYDROPHOBIC MODIFICATION FOR CONTROLLED CROSSLINKING OF LATEX POLYMERS

(71) Applicant: Ennis Paint, Inc., Thomasville, NC (US)

(72) Inventor: Haibo Li, High Point, NC (US)

(73) Assignee: Ennis Paint, Inc., Thomasville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/943,903

(22) Filed: Nov. 17, 2015

(65) Prior Publication Data

US 2016/0208129 A1 Jul. 21, 2016

Related U.S. Application Data

(63) Continuation of application No. 14/600,822, filed on Jan. 20, 2015, now Pat. No. 9,499,714.

(51) Int. Cl.

| C09D 133/12 | (2006.01) |
|---|---|
| C08K 5/3492 | (2006.01) |
| C09D 153/02 | (2006.01) |
| C09D 5/02 | (2006.01) |
| C07D 251/30 | (2006.01) |
| C08F 220/14 | (2006.01) |
| E01F 9/518 | (2016.01) |
| C07C 209/68 | (2006.01) |
| C07C 215/08 | (2006.01) |
| C07C 227/02 | (2006.01) |
| C07C 229/16 | (2006.01) |
| C07D 403/14 | (2006.01) |
| C09D 5/14 | (2006.01) |
| C08G 59/14 | (2006.01) |
| C09D 7/63 | (2018.01) |
| C09D 5/00 | (2006.01) |
| C08K 5/103 | (2006.01) |
| C08K 5/17 | (2006.01) |

(52) U.S. Cl.
CPC .......... *C08K 5/3492* (2013.01); *C07C 209/68* (2013.01); *C07C 215/08* (2013.01); *C07C 227/02* (2013.01); *C07C 229/16* (2013.01); *C07D 251/30* (2013.01); *C07D 403/14* (2013.01); *C08F 220/14* (2013.01); *C08G 59/1477* (2013.01); *C08K 5/34924* (2013.01); *C08K 5/34926* (2013.01); *C09D 5/024* (2013.01); *C09D 5/14* (2013.01); *C09D 7/63* (2018.01); *C09D 133/12* (2013.01); *C09D 153/02* (2013.01); *E01F 9/518* (2016.02); *C08K 5/103* (2013.01); *C08K 5/17* (2013.01); *C08K 5/175* (2013.01); *C09D 5/00* (2013.01)

(58) Field of Classification Search
CPC ...... C08L 63/00; C08L 77/10; C08L 2312/00; C08J 2463/02
See application file for complete search history.

(56) References Cited

U.S. PATENT DOCUMENTS

| 3,673,022 | A | * | 6/1972 | Iwami | ........................ C08J 5/06 156/166 |
|---|---|---|---|---|---|
| 3,704,281 | A | * | 11/1972 | Saran et al. | ........... C08G 59/10 525/523 |
| 4,265,745 | A | | 5/1981 | Kawaguchi et al. | |
| 5,681,907 | A | | 10/1997 | Starner et al. | |
| 9,499,714 | B2 | * | 11/2016 | Li | ........................ C09D 133/12 |

OTHER PUBLICATIONS

USPTO structure search, Feb. 2017.*
Guerink, Pieter JA, et al. Analytical aspects and film properties of two pack acetoacetate functional latexes. Progress in Organic Coatings, 1996, 27.1: 73-78.
Israel Patent Office. International Search Report for PCT/US2015/061128. dated Apr. 17, 2016. Jerusalem, Israel.

\* cited by examiner

*Primary Examiner* — Gregory Listvoyb
(74) *Attorney, Agent, or Firm* — Kilpatrick Townsend & Stockton LLP

(57) ABSTRACT

Polyfunctional amine structures exhibiting at least one hydrophobic moiety selected from the group consisting of; hydrophobic epoxides, hydrophobic glycidyl ethers and hydrophobic (meth)acrylates are described which provide crosslinking capabilities for latex polymer compositions. These crosslinkers not only exhibit latent crosslinking properties but also improved hydrophobicity when compared with existing latex formulations. Latent crosslinking provides advantages associated with fast interactions between the anionic latex charge and the cationic charge associated with these hydrophobically modified polyfunctional amine crosslinkers. Once the latex is coated onto a substrate, the volatile base evaporates and the groups react to form a crosslinked coating with both improved hydrophobic and wash-off properties.

4 Claims, No Drawings

POLYFUNCTIONAL AMINES WITH HYDROPHOBIC MODIFICATION FOR CONTROLLED CROSSLINKING OF LATEX POLYMERS

PRIORITY

This application is a continuation application of U.S. Nonprovisional application Ser. No. 14/600,822 filed Jan. 20, 2015 and entitled "Controlled Crosslinking of Latex Polymers with Polyfunctional Amines" the entire contents of which are also hereby incorporated by reference.

BACKGROUND

This disclosure covers the field of emulsion chemistry. In particular, it relates to distinct solution based polymerized latex compositions that are initially shelf stable emulsions prior to being used as coatings and/or paints. More specifically these latex compositions are kept shelf stable in the presence of a specific amount of ammonium hydroxide to maintain high pH in order to avoid premature interaction (pre-gelling) between latex particles leading to settling, and both inter and/or intraparticle crosslinking of the latex binders. These solutions are ammonia ($NH_3$) rich (using ammonium hydroxide) and thus highly basic; therefore, when the $NH_3$ evaporates quickly, the pH of the solutions are reduced as they are applied to surfaces. This process serves as a trigger for controlled crosslinking of the latex (binder) as it interacts with the polyfunctional amines of the present disclosure during application and drying. The pursuit of fast drying aqueous traffic paints requires there be strong and effective interactions between the latex binder and water-soluble polyfunctional amine crosslinkers, to ensure fast hardening at proper high build (in a single coat thick application) translating into corresponding water resistance.

In an increasing number of industries, aqueous coating compositions continue to replace traditional organic solvent-based coating compositions. Paints, inks, sealants, and adhesives, for example, previously formulated with organic solvents are now formulated as aqueous compositions. This reduces potentially harmful exposure to volatile organic compounds (VOC's) commonly found in solvent-based compositions. Migration from organic solvent-based to aqueous compositions allows for health and safety benefits, however, the aqueous coating compositions must meet or exceed the performance standards expected from solvent-based compositions. The need to meet or exceed the organic solvent based performance standards places a premium on the characteristics and properties of waterborne polymer compositions used in aqueous coating compositions.

The latex industry and specifically the latex-based traffic paint products have historically held a long established goal of developing effective "one-pack" (proper high build-in a single coat thick application)—or single step crosslinking systems. The ideal system allows for film formation prior to substantial crosslinking as the latex is applied to surfaces. The nature of this coating technology requires that it is stable when being stored and fast drying only when being applied. The structural make-up of these aqueous systems must be unreactive in the wet state, but very capable of ionic bonding (in ambient conditions) in the dry state; referred to hereinafter as latent crosslinking. The result of latent crosslinking would be a good film-forming latex with excellent hardness that is very resistant to water wash-off.

Much published art regarding various "one-pack" chemistries exists, including those based on epoxies (specifically glycidyl methacrylate), silanes, isocyanates, and carbonyls (including acetoacetoxy ethyl methacrylate, and acetoacetoxyethyl methacrylate-AAMA). Most of these publications and/or granted patents have demonstrated the presence of crosslinking by showing improved solvent resistance.

In order to increase the potlife (or shelf stability) of compositions containing acetoacetate and amine groups it has been known to block the amine groups of the polyamine with a ketone or aldehyde to form corresponding ketimine or aldimine compounds prior to mixing with an acetoacetate-functional polymer. Examples of such non-aqueous compositions are disclosed in U.S. Pat. No. 4,772,680. Even though improved stability may be achieved by specific aromatic aldimines, volatile by-products are still formed and the compositions have no application in waterborne coatings and are restricted to coatings using organic solvents as the carrier.

WO 95/09209 describes a crosslinkable coating composition comprising an aqueous film forming dispersion of addition polymer comprising acetoacetate functional groups and an essentially non-volatile polyamine having at least two primary amine groups and wherein the mole ratio of acetoacetate to primary amine groups is between 1:4 to 40:1.

EP 555,774 and WO 96/16998 describe the use of carboxylated acetoacetoxyethyl methacrylate latexes mixed with multifunctional amines (such as diethylene triamine) for a shelf-stable, one-component system. In EP 555,774, the system is stabilized by using vinyl acid polymerized with AAEM and the latex is "neutralized" with a polyamine. The patent teaches that the carboxyl groups should be 70 to 96 mol percent relative to the acetoacetoxy groups. WO 96/16998 similarly describes a polymerization process with the vinyl acid and AAEM being polymerized in the first stage.

EP 744,450 describes aqueous coating compositions containing acetoacetate functional polymers with a weight-averaged molecular weight of 100,000 or greater and which contain acetoacetate functional groups and acidic functional groups, and multifunctional amine.

EP 778,317 describes an aqueous self-crosslinkable polymeric dispersion comprising a polymeric component (a relatively hydrophobic polymer having a Hansch number >1.5, at least 5% of a carbonyl functional group capable of reacting with a nitrogen moiety, and at least 1% of a non-acidic functional group having hydrogen-bondable moieties); and a crosslinking agent comprising a nitrogen-containing compound having at least two nitrogen functional groups capable of reacting with a carbonyl functional moiety. Again it is reported that no gelation has taken place after ten days at 60° C.

U.S. Pat. No. 5,498,659 discloses a single-package aqueous polymeric formulation consisting essentially of an evaporable aqueous carrier, at least one polymeric ingredient having acid-functional pendant moieties able to form stable enamine structures, a non-polymeric polyfunctional amine having at least two amine functional moieties, and an effective amount of base for inhibiting gelation. It is stated in the patent that at least some of the crosslinking of the composition may take place in the liquid phase, possibly within one to four hours of adding the non-polymeric polyfunctional amine. It is postulated that addition of base to the reactor contents competes with the amine-functional moieties vis-à-vis the acetoacetoxy-type functional moieties, thereby reducing the degree of crosslinking and/or enhancing the colloidal stability of the polymer dispersion which forms when the crosslinking reaction takes place.

Geurink, et al., in their publication "Analytical Aspects and Film Properties of Two-Pack Acetoacetate Functional Latexes", Progress in Organic Coatings 27 (1996) 73-78, report that crosslinking of acetoacetate functional latexes with polyamine compounds is very fast, and that this crosslinking is hardly hindered by existing enamines. It is further stated that there are very strong indications that crosslinking takes place rapidly in the wet state, in or at the surface of the particles just after mixing of the components. They conclude that as a result of crosslinking in the particles, the film forming process is hampered.

In the publications described above, the usable pot life of the latex formulations is demonstrated by lack of sedimentation. It is quite possible, however, that crosslinking is taking place within each particle, without causing the latex to coagulate or gel (e.g. loss of colloidal stability). This type of intra-particle crosslinking (before drying) limits the ability of the latex to form a film upon drying. This in turn reduces the film integrity and performance of the polymer. Therefore, a need still exists for truly latent crosslinking systems—those in which intraparticle crosslinking is inhibited until after film formation. In particular, a need exists for one-pack, latent crosslinking systems which are useful in a wide range of latex applications that are simple and cost efficient. These would include decorative and protective coatings, adhesives, non-woven binders, textiles, paper coatings, traffic markings, inks, etc. In each case, the advantage would be a soft, ductile polymer that converts to a harder, more resistant latex film after drying.

In general, the following acronyms are used throughout the body this specification and provide information regarding chemical compounds and structures as follows;
ADS=ammonium dodecyl sulfate
APS=ammonium persulfate
BA=butyl acrylate
DMAPA=N,N-dimethyl amino propyl amine.
MMA=methyl methacrylate
MAA=methacrylic acid
PEI=polyethyleneimine
SDS=sodium dodecyl sulfate
tBHP=t-butyl hydroperoxide
TGIC=Triglycidyl isocyanurate

SUMMARY

Amine linkers are water soluble polyfunctional amines promoting interaction among cationic latex particles when the pH and solid content of the dispersion media changes. However since latex polymers are essentially hydrophobic, the intrinsic hydrophilic nature of the polyfunctional amine makes it difficult for fusion of the latex particles to happen in a timely manner. When coalescence among latex particles occurs, behavior of the hydrophilic amine linkers acts as a barrier preventing inter-diffusion of polymer chains into different latex particles. This fact results in slowing film formation of the paint composition and its corresponding water resistance.

The introduction of hydrophobic groups to polyfunctional amine crosslinkers is achieved via post-modification using acrylate or hydrophobic epoxy reactants. Here a polyfunctional amine can be defined as any molecule possessing at least 3 pH responsive amino nitrogen atoms. The post modification of amine linkers is achieved by reaction between the residual —NH or —NH2 groups with the post modifying agent, including hydrophobic epoxy chemicals, hydrophobic glycidyl ethers and (meth)acrylates. The modification reactions can be carried out at ambient temperature and pressure.

A first aspect of the present disclosure includes polyfunctional amine crosslinkers comprising recurring units derived from the reaction of one tri-glycidyl moiety and a single di-, or tri-functional amino monomers, or combination of mono/tri, mono/tetra, bi/bi, bi/tri, bi/tetra, tri/tri, tri/tetra, and tetra/tetra functional amino monomers resulting in a polyfunctional amine of formula (I-x):

$$-\!\!\left[\!\!\begin{array}{c}R1\\|\\J-R2\end{array}\!\!\right]_{\!n}\!\!-\quad\text{(I-x)}$$

Where the substituent J is the result of a ring-opening reaction during nucleophilic substitution of a bi- or tri-glycidyl moiety;

and wherein R1 is selected from the group consisting of: methyl amine, ethyl amine, 1-propyl amine, ethanol amine, 2-propyl amine, 1-butyl amine, 2-butyl amine, 2-methyl-2-propyl amine, piperazine, N,N-dimethyl-ethyl diamine, N,N-diethyl-ethyl diamine, N,N-dimethyl propyl diamine, N,N-diethyl-propyl diamine, N,N-dimethyl amino propylamine, N,N-dimethyl ethylene amine, N,N-diethyl amino propylene amine, N,N-diethylamino ethylene amine, amino ethyl-piperazine, N-methyl-1,2-ethane diamine, N-ethyl-1,2-ethane diamine, N-methyl-1,3-propane diamine, N-ethyl-1,3-propane diamine, 1,2-diamine ethane, 1,3-diamino propane, 1,4-diamino butane, cadaverine, cystamine, 1,6-diamino hexane, 1,2-diamine benzene, 1,3-diamino benzene, 1,4-diamino benzene, 1,4-diamino butanol, 4,4-diamino-3-hydroxy butanoic acid, 5-amino-1,3,3-trimethyl-cyclohexanemethylamine, 2,2'-oxybis ethanamine, alanine, and lysine;

and wherein R2 is selected from group consisting of: methyl amine, ethyl amine, 1-propyl amine, ethanol amine, 2-propyl amine, 1-butyl amine, 2-butyl amine, 2-methyl-2-propyl amine, piperazine, N,N-dimethyl-ethyl diamine, N,N-diethyl-ethyl diamine, N,N-dimethyl propyl diamine, N,N-diethyl-propyl diamine, N,N-dimethyl amino propylamine, N,N-dimethyl ethylene amine, N,N-diethyl amino propylene amine, N,N-diethylamino ethylene amine, amino ethyl-piperazine, N-methyl-1,2-ethane diamine, N-ethyl-1,2-ethane diamine, N-methyl-1,3-propane diamine, N-ethyl-1,3-propane diamine, 1,2-diamine ethane, 1,3-diamino propane, 1,4-diamino butane, cadaverine, cystamine, 1,6-diamino hexane, 1,2-diamine benzene, 1,3-diamino benzene, 1,4-diamino benzene, 1,4-diamino butanol, 4,4-diamino-3-hydroxy butanoic acid, 5-amino-1,3,3-trimethyl-cyclohexanemethylamine, 2,2'-oxybis ethanamine, alanine, lysine;

and where R1 is equal to or different than R2;
and where n is a number from 10 to 100.

More specifically, the polyfunctional amines are selected from one of the general structures of formulae (I-x) and/or (I-x-a) to (I-x-f):

$$-\!\!\left[\!\!\begin{array}{c}R1\\|\\J-R2\end{array}\!\!\right]_{\!n}\!\!-\quad\text{(I-x)}$$

-continued

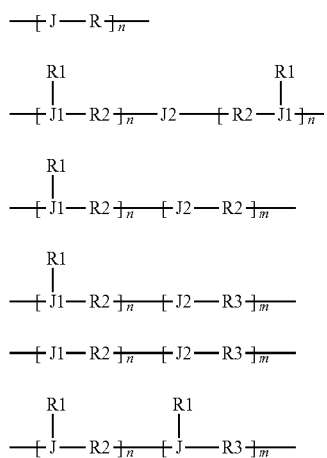

(I-x-a)
(I-x-b)
(I-x-c)
(I-x-d)
(I-x-e)
(I-x-f)

wherein substituents J, J1, and J2 are the result of a ring-opening reaction during nucleophilic substitution of a bi- or tri-glycidyl moiety;

and wherein J is equal to or different than J1 and J2;

and wherein J1 is equal to or different than J2;

and wherein R1 is selected from the group consisting of: methyl amine, ethyl amine, 1-propyl amine, ethanol amine, 2-propyl amine, 1-butyl amine, 2-butyl amine, 2-methyl-2-propyl amine, piperazine, N,N-dimethyl-ethyl diamine, N,N-diethyl-ethyl diamine, N,N-dimethyl propyl diamine, N,N-diethyl-propyl diamine, N,N-dimethyl amino propylamine, N,N-dimethyl ethylene amine, N,N-diethyl amino propylene amine, N,N-diethylamino ethylene amine, amino ethyl-piperazine, N-methyl-1,2-ethane diamine, N-ethyl-1,2-ethane diamine, N-methyl-1,3-propane diamine, N-ethyl-1,3-propane diamine, 1,2-diamine ethane, 1,3-diamino propane, 1,4-diamino butane, cadaverine, cystamine, 1,6-diamino hexane, 1,2-diamine benzene, 1,3-diamino benzene, 1,4-diamino benzene, 1,4-diamino butanol, 4,4-diamino-3-hydroxy butanoic acid, 5-amino-1,3,3-trimethyl-cyclohexanemethylamine, 2,2'-oxybis ethanamine, alanine, and lysine;

and R2 and R3 are selected from group consisting of: methyl amine, ethyl amine, 1-propyl amine, ethanol amine, 2-propyl amine, 1-butyl amine, 2-butyl amine, 2-methyl-2-propyl amine, piperazine, N,N-dimethyl-ethyl diamine, N,N-diethyl-ethyl diamine, N,N-dimethyl propyl diamine, N,N-diethyl-propyl diamine, N,N-dimethyl amino propylamine, N,N-dimethyl ethylene amine, N,N-diethyl amino propylene amine, N,N-diethylamino ethylene amine, amino ethyl-piperazine, N-methyl-1,2-ethane diamine, N-ethyl-1,2-ethane diamine, N-methyl-1,3-propane diamine, N-ethyl-1,3-propane diamine, 1,2-diamine ethane, 1,3-diamino propane, 1,4-diamino butane, cadaverine, cystamine, 1,6-diamino hexane, 1,2-diamine benzene, 1,3-diamino benzene, 1,4-diamino benzene, 1,4-diamino butanol, 4,4-diamino-3-hydroxy butanoic acid, 5-amino-1,3,3-trimethyl-cyclohexanemethylamine, 2,2'-oxybis ethanamine, alanine, lysine;

and wherein R1 is equal to or different than R2 and R3;

and wherein R2 is equal to or different than R3;

and where n is an number 1 to 100;

and where m is an number equal to or different than n;

and wherein said I-x structure is represented as I-x-2';

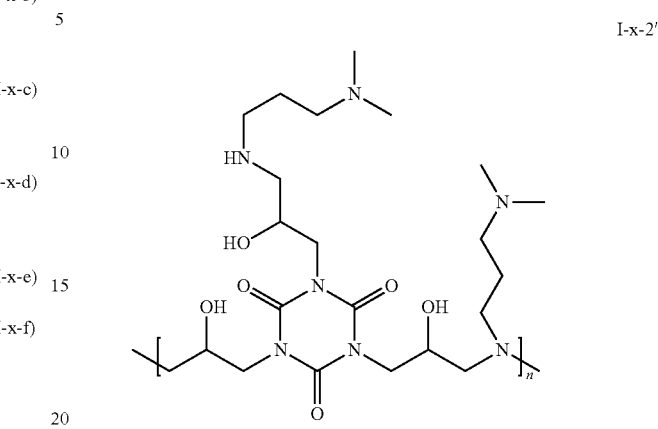

I-x-2' and wherein the polyfunctional amine of any of formulae (I-x) and/or (I-x-a) to (I-x-f) must also include at least three pH responsive amino group sites and additionally, at least one —NH and/or one —NH2 site providing reactive sites for hydrophobic compounds thereby introducing at least one hydrophobic moiety as represented by structures of formulae I-x-2'a, I-x-2'b, I-x-2'c and I-x-2'd, all of which are hydrophobic modifications of I-x-2';

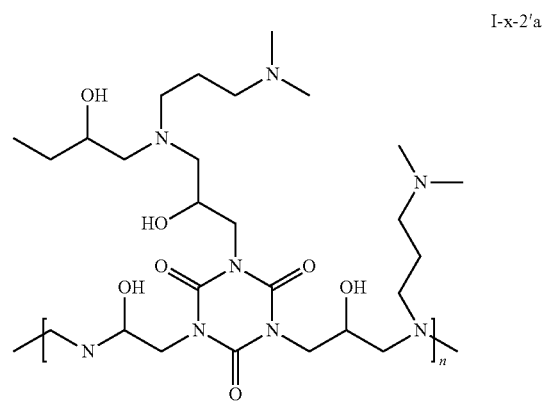

I-x-2'a

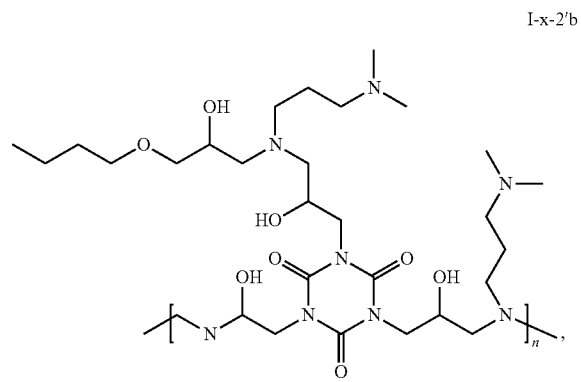

I-x-2'b

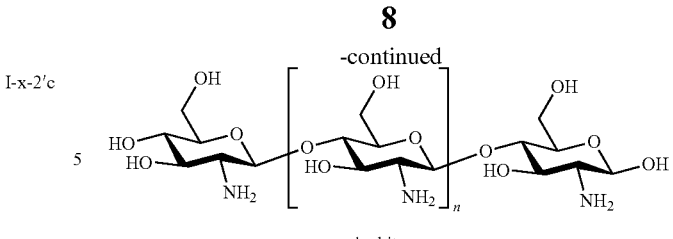

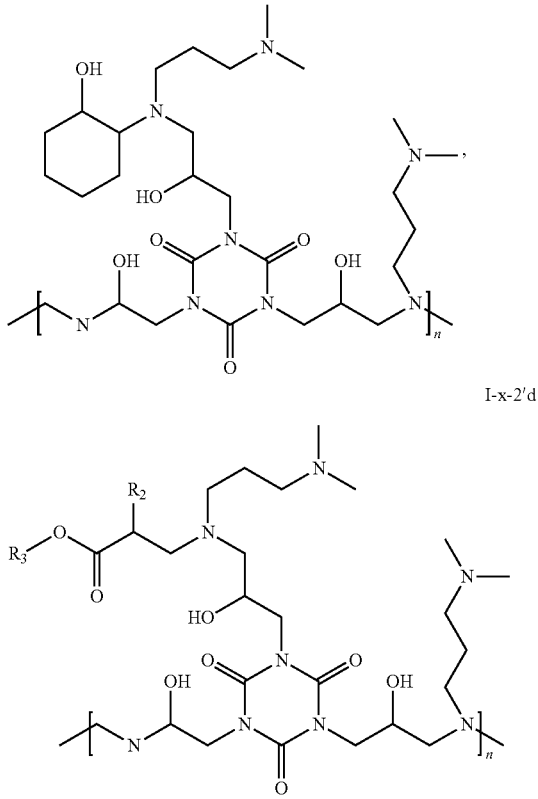

The focus of the present disclosure includes the introduction of hydrophobic groups to I-x and subsequently to I-x-a to I-x-f structures where it is possible to also include by reactions with the following group classifications;

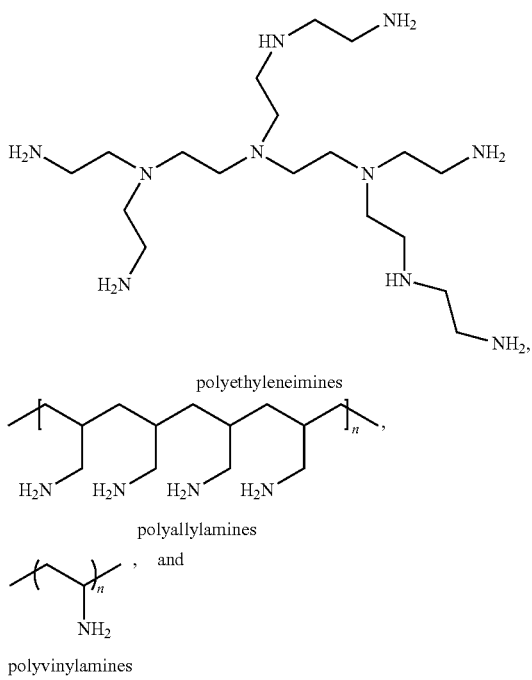

for establishing crosslinkers as starting compounds which can be altered via post-modification reactions with acrylate or hydrophobic epoxy reactants. The post modification of these crosslinkers is achieved by a reaction between the residual —NH or —NH2 groups and with the post modifying reactants. These reactants include hydrophobic epoxy groups and hydrophobic glycidyl ethers and (meth)acrylate groups.

The initial glycidyl/amino polyfunctional amine latex crosslinker composition (I-x-2') is selected from at least one compound from the group consisting of Formulae (I-x) and/or (I-x-a to I-x-f as shown above), composed of a bi- or tri-glycidyl moiety and amine(s) group(s). This structure is developed from a one-step Reaction Type I process resulting in (I-x-2') products (structural compounds) and does not include any —C=C— bonds.

It should also be noted that the Reaction Type I, I-x-2' compound can be utilized "as is" with no further treatment and will function as a polyfunctional amine crosslinker without hydrophobic modification. In addition, polyfunctional amine (I-x-2') compounds (containing either —NH or —NH$_2$ moieties) can be further treated to form hydrophobically modified polyfunctional amine crosslinkers.

The polyfunctional amines of the present disclosure are a result of a condensation reaction of a glycidyl groups with an amine groups reacting together to provide for example I-x-2'. Other starting components, which can be reacted with hydrophobic moieties (hydrophobic epoxy groups, hydrophobic glycidyl ethers, and (meth)acrylate groups) include polyethyleneimines, polyallylamines, polyvinylamines, and polychitosans. In this case the resulting polyfunctional amines comprise at least three separate amino groups that are pH responsive and will accept or release proton(s) in response to a change in pH.

8. A general synthetic process comprising providing one or more hydrophobically modified polyfunctional amine crosslinkers that are also Quick Drying Agents (QDAs) via a Type II reaction comprising a reaction schema;

(PEI)+(Y)→(QDA-Y)

by reacting reactants polyethylene amine (PEI) and a hydrophobic moiety (Y) including a hydrophobic epoxide (C) such as 1-butene oxide, a glycidyl ether (D) such as butyl glycidyl ether (BGE), a ringed hydrocarbon based oxide such as cyclohexene oxide (E), and an acrylic monomer emulsion (F) resulting in producing QDA-Y products.

The polyfunctional amines, as described herein can be used in latex paint formulas as crosslinkers. Complete paint formulations utilizing both a latex and one or more polyfunctional amines, or a combination of polyfunctional amines, as described and provided herein are also subjects of the present disclosure.

The paint formulation wherein both a latex and the polyfunctional amines of the present invention are combined is another embodiment of the present specification.

The paint formulation may additionally include at least one member of the group consisting of; dispersants, defoamers, surfactants, biocides, ammonia, rheology agents, pigments, solvents, coalescents, and water.

The paint formulation is used as traffic paint for a pavement surface.

The paint formulation is paint applied to pavement surfaces such that crosslinking of the paint occurs and the paint dries within 15 minutes so that no early water wash-off can occur. Additionally, when the paint formulation is applied to pavement surfaces, crosslinking of the latex paint composition occurs leading to early water resistance which occurs within 8-12 minutes.

The polyfunctional amines are a result of a condensation reaction of one or more glycidyl groups with one or more amine groups and wherein resulting polyfunctional amines comprise at least three separate amino groups that are pH responsive in that said the amino groups accept or release proton(s) in response to a change in pH.

The polyfunctional amines of the present disclosure wherein the polyfunctional amines provide an ability to tailor the final molecular weight of said the polyfunctional amines.

In a separate embodiment, the one or more polyfunctional amine latex compositions of the present disclosure wherein the compositions are crosslinking agents represented by formula (I-x) which when bearing —NH or —NH$_2$ groups with repeating units, n, are further reacted with glycidyl alkyl either or alkyl epoxy compounds, and wherein polyfunctional amines of any of formulae (I-x) and/or (I-x-a) to (I-x-f) further include —NH or —NH$_2$ groups that are also further reacted with glycidyl alkyl ether or alkyl epoxy compounds such that introduction of one or more hydrophobic groups form hydrophobically modified crosslinking agents (I-x-2'a), (I-x-2'b), (I-x-2'c) and I-x-2'd);

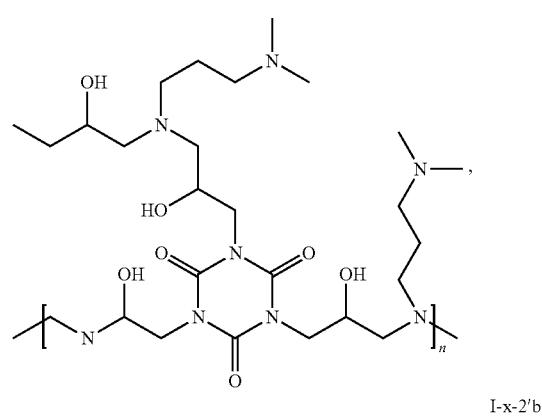

I-x-2'a

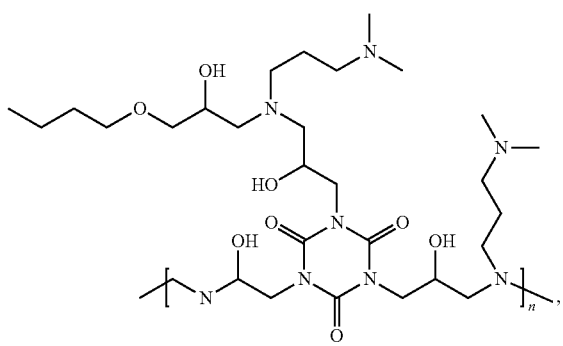

I-x-2'b

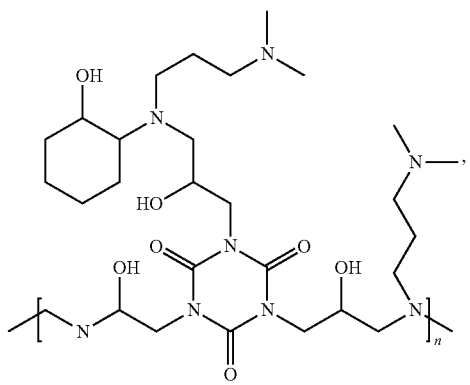

I-x-2'c

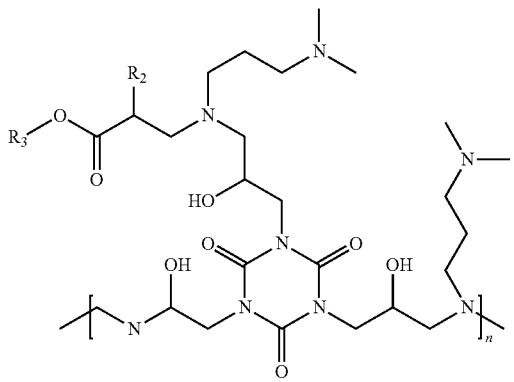

I-x-2'd wherein introduction of these compounds to the structure of formula (I-x) occurs only once per repeating unit, n, thereby creating a repeating unit of n−1 when treated with additional polyfunctional amines.

DETAILED DESCRIPTION

The present invention provides polyfunctional amine crosslinkers for use in latex polymer compositions and the latex polymer compositions containing them. The latex polymer compositions of the present invention typically include, but are not limited to, latexes, dispersions, microemulsions, or suspensions. The latex polymer compositions of the present invention may be stored at room temperature or moderately above room temperature (e.g., about 50 to 60° C.) and provide adhesion and crosslinking upon film formation when applied to a substrate. A film or coating formed with polymers of the present invention may be cured at room temperature (ambient cure) or at elevated temperatures (thermal cure).

The latex polymer binders used to prepare the waterborne polymer composition of the present disclosure are generally prepared as particles. The particles may be structured or unstructured. Structured particles include, but are not limited to, core/shell particles and gradient particles. The average polymer particle size may range from about 100 to about 300 nm.

The polymer particles have a spherical shape. In one embodiment, the spherical polymeric particle may have a core portion and a shell portion. The core/shell polymer particles may also be prepared in a multi-lobe form, a peanut shell, an acorn form, or a raspberry form. It is further preferred in such particles that the core portion comprises about 20 to about 80 of the total weight of said particle and the shell portion comprises about 80 to about 20 of the total weight volume of the particle.

The present disclosure includes compositions and methods for the preparation of water soluble polyfunctional amines for use as crosslinking agents in solutions of fast drying latex emulsions and the further modification of these crosslinkers for use as hydrophobic crosslinking agents in solutions of fast drying latex emulsions. The oligomeric/polymeric polyfunctional amine synthesized in a Reaction Type I process by reacting bi- or tri-functional glycidyl and/or glycidyl isocyanurate groups with water soluble bi-, tri- and tetra-amines as the starting materials (reactants) serve as crosslinkers for latex paints. The resulting Reaction Type I process polyfunctional amines can be combined with epoxy, acrylic, and glycidyl ether compounds in a post-modification Reaction Type II process to form hydrophobic compounds. The Reaction Type II processes can be carried out without the selection of Reaction Type I compounds such as I-x-2'. The use of polyethyleneimine, polyallylamine, polyvinylamine, and/or polychitosan as the starting material in a direct reaction with hydrophobic moieties (hydrophobic epoxy groups and hydrophobic glycidyl ethers and (meth)acrylate groups) without post modification is also possible. The determination of whether the resulting chemical compound structures are an oligomer or polymer depends on the final weight average molecular weight (as determined primarily by the number and molecular weight) of the repeating structural monomeric chains.

The fast drying and proper curing due to crosslinking of the latex emulsion is triggered by rapid evaporation of $NH_3$ in the paint formulation concurrent with a rise in the pH of the emulsion during and after being applied to the intended surface. The interaction of the latex binder together with the hydrophobically modified crosslinking polyfunctional amine (primarily) oligomers results in fast dry traffic latex polymers (as paints or coatings) which harden quickly. These polymeric/oligomeric amines provide for adequate water (especially rain water) resistant films due in part due to their rapid cure times. The waterborne fast dry paint serves as road and pavement marking paint which can be used to mark lines or symbols on roads, parking lots, and walkways etc.

The synthesis of the crosslinkers of the present disclosure can be completed utilizing either a Reaction Type I or Reaction Type II process. The Reaction Type I process provides crosslinkers resulting from the reactions using glycidyl monomer(s) and/or amino monomer(s). The Reaction Type II process provides crosslinkers of the Reaction Type I process that have been further reacted with hydrophobic groups resulting in structures containing hydrophobic moieties. Examples of hydrophobically modified crosslinkers which do not employ the use of glycidyl/amino monomers of the Reaction Type I process can be used in the Reaction Type II process with the proviso that there are at least three or more amino nitrogen groups available for bonding with the chosen hydrophobic moiety that are pH responsive and will accept or release proton(s) in response to a change in pH. Examples of hydrophobically modified crosslinkers not employing the use of glycidyl/amino monomers of the Reaction Type I process include starting materials including polyethyleneimines, polyallylamines, polyvinylamines, and polychitosans.

Selection of Monomers

Triglycidyl isocyanurate is the trifunctional glycidyl monomer used in the present disclosure. Diglycidyl monomers include: poly(propylene glycol)diglycidyl ether, poly (ethylene glycol)diglycidyl ether, resorcinol glycidyl ether, neopentyl diglycidyl ether, and butanediol diglycidyl ether. The glycidyl monomer(s) employed in the disclosure can be used singularly or in combination.

Amine monomers employed in this work can be bi-, tri- or tetra-monomers or combinations of, mono/tri, mono/tetra, bi/bi, bi/tri, bi/tetra, tri/tri, tri/tetra and tetra/tetra functional monomers. In amine monomers, the number of functionalities is defined by the number of N—H bonds.

A full list of mono-functional amine monomers include: dimethyl amine, diethyl amine, diethanol amine, dipropyl amine, pyrrolidine, piperidine, 1-methyl piperazine, N,N,N-trimethyl-1,2-ethane diamine, N,N,N, triethyl-1,2-ethane diamine, N-methyl-N,N-diethyl-1,2-ethane diamine, N-ethyl-N,N-dimethyl-1,2-ethane diamine, N-methyl-N,N-diethyl-1,3-propane diamine, and N-ethyl-N,N-dimethyl-1, 3-propane diamine, A full list of bi-functional amine monomers includes: methyl amine, ethyl amine, 1-propyl amine, ethanol amine, 2-propyl amine, 1-butyl amine, 2-butyl amine, 2-methyl-2-propyl amine, piperazine, N,N-dimethyl-ethyl diamine, N,N-diethyl-ethyl diamine, N,N-dimethyl propyl diamine, N,N-diethyl-propyl diamine, N,N-dimethyl amino propylamine, N,N-dimethyl ethylene amine, N,N-diethyl amino propylene amine, and N,N-diethylamino ethylene amine.

A full list of tri-functional amine monomers includes: amino ethyl-piperazine, N-methyl-1,2-ethane diamine, N-ethyl-1,2-ethane diamine, N-methyl-1,3-propane diamine, and N-ethyl-1,3-propane diamine.

A full list of tetra-functional amine monomers includes: 1,2-diamine ethane, 1,3-diamino propane, 1,4-diamino butane, cadaverine, cystamine, 1,6-diamino hexane, 1,2-diamine benzene, 1,3-diamino benzene, 1,4-diamino benzene, 1,4-diamino butanol, 4,4-diamino-3-hydroxy butanoic acid, 5-amino-1,3,3-trimethylcyclohexanemethylamine, 2,2'-oxybis ethanamine, alanine, and lysine.

Type I Reactions: Glycidyl/Amino Polyfunctional Amines (I-x-Ib-12')

A first aspect of the present disclosure involves starting with polyfunctional amine crosslinkers comprising recurring units derived from the reaction of one tri-glycidyl moiety and a single di-, or tri-functional amino monomer, or combination of mono/tri, mono/tetra, bi/bi, bi/tri, bi/tetra, tri/tri, tri/tetra and tetra/tetra functional amino monomers resulting in a polyfunctional amine of the general formula 0-4

(I-x)

Where the substituent J is the result of a ring-opening reaction during nucleophilic substitution of a bi- or tri-glycidyl moiety;

and wherein R1 is selected from the group consisting of all possible mono-functional, bi-functional, tri-functional or tetra-functional amines, as provided above;

and wherein R2 is selected from the group of all possible bi-functional, tri-functional or tetra-functional amines;

and where R1 is equal to or different than R2;

and where n is a number 1 to 100.

Further possible structures for providing polyfunctional amines using a Reaction Type I process are provided in general formulae (I-x) and/or (I-x-a) to (I-x-f):

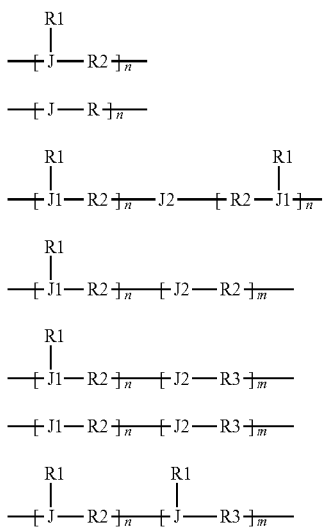

(I-x)

(I-x-a)

(I-x-b)

(I-x-c)

(I-x-d)

(I-x-e)

(I-x-f)

Where the substituents J, J1, and J2 are the result of a ring-opening reaction during nucleophilic substitution of a bi- or tri-glycidyl moiety, and wherein J is equal to or different than J1 and J2;

and wherein J1 is equal to or different than J2;

and wherein R1 is selected from the group consisting of all possible mono-functional, bi-functional, tri-functional or tetra-functional amines;

and wherein R2 and R3 are selected from group consisting of all possible bi-functional, tri-functional or tetra-functional amines and wherein R1 is equal to or different than R2 and R3;

and wherein R2 is equal to or different than R3;

and where n is an number 1 to 100;

and where m is an number equal to or different than n and wherein said I-x structure is represented as I-x-2';

I-x-2'

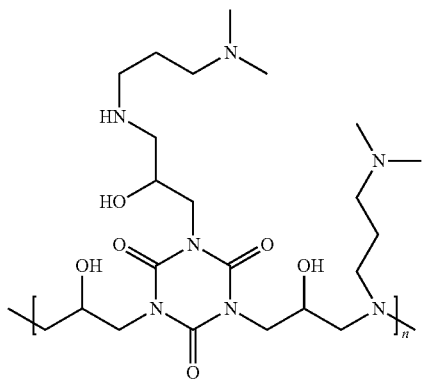

and wherein the polyfunctional amine of any of formulae (I-x) and/or (I-x-a) to (I-x-f) must also include at least three pH responsive amino group sites and additionally, at least one —NH and/or one —NH2 site providing reactive sites for hydrophobic compounds thereby introducing at least one hydrophobic moiety as represented by structures of formulae I-x-2'a, I-x-2'b, I-x-2'c and I-x-2'd, all of which are hydrophobic modifications of I-x-2';

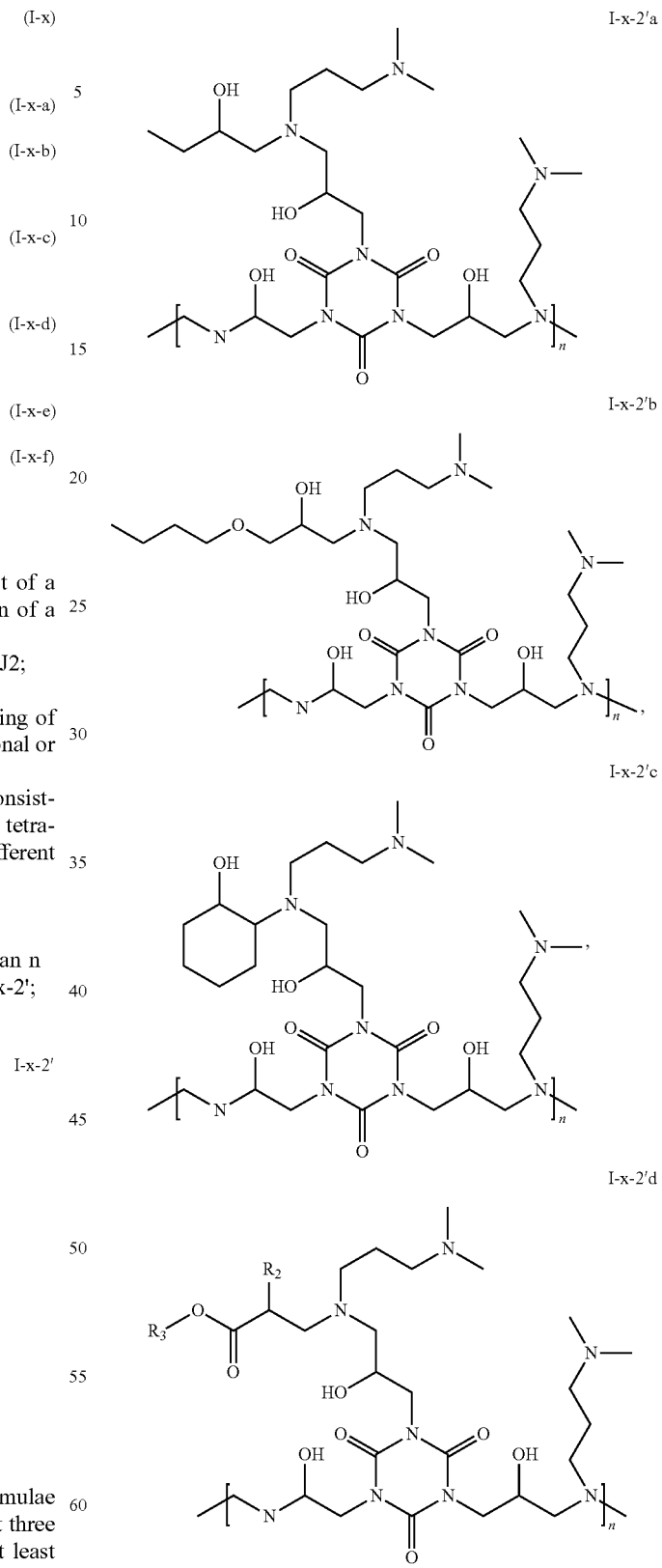

For the Reaction Type I synthesis of polyfunctional amines, it is possible to provide a combination of amines. The combination can be mono/tri, mono/tetra or bi/bi, bi/tri, bi/tetra, tri/tri, tri/tetra and tetra/tetra for tri-glycidyl monomer, and can be bi/bi, bi/tri, bi/tetra, tri/tri, tri/tetra and tetra/tetra for bi-glycidyl monomer. Combinations of mono/mono will not provide the required moieties for the present disclosure.

To make the reactions in the current disclosure work, proper ratios of glycidyl monomers to amine monomers and ratios among all amines when combinations of amines are involved and ratios among all glycidyl monomers when combinations of glycidyl monomers are used, need to be controlled. The following relations have to be true for construction of desired polyamine in this disclosure:

1. Reaction between triglycidyl monomer and single bi, tri and tetra amines, or combinations of bi/bi, bi/tri, bi/tetra, tri/tri, tri/tetra and tetra/tetra amines:

$M_a/M_g = 2n+1$

2. Reaction between triglycidyl monomer and combination of mono/tri amines $M_a/M_g = 2n+1$, and $2M_{tria}/M_g \geq 1-1/n$ 3. Reaction between triglycidyl monomer and combination of mono/tetra amines $M_a/M_g = 2n+1$, and $3M_{tetra}/M_g \geq 1-1/n$ 4. Reaction between biglycidyl monomer/combination of biglycidyl monomers and single bi, tri, tetra amines, or combinations of bi/bi, bi/tri, bi/tetra, tri/tri, tri/tetra and tetra/tetra amines:

$M_a/M_g = n+1$

5. Reaction between biglycidyl monomer/combination of biglycidyl monomers and combination of mono/tri amines:

$M_a/M_g = n+1$, and $2M_{tria}/M_g \geq 1-1/n$

6. Reaction between biglycidyl monomer/combination of biglycidyl monomers and combination of mono/tetra amines:

$Ma/Mg = n+1$, and $3Mt_{etraa}/M_g \geq 1-1/n$

Where: $M_a$: molar amount of total amine used in reaction.
$M_g$: molar amount of total glycidyl monomer used in reaction.
$M_{tria}$: molar amount of total triamine used in reaction.
$M_{tetraa}$: molar amount of total tetraamine used in reaction.
n: designed polymerization degree of polyfunctional amine.

Type II Reaction: Hydrophobic Modification of Polyfunctional Amines

Oligomeric Reaction Type I polyfunctional amines can be prepared from the reaction between tri-glycidyl monomer and a bi, a tri-, and/or a tetra functional amine, or combinations of bi/bi, bi/tri, bi/tetra, tri/tri, tri/tetra and tetra/tetra amines, or between bi glycidyl monomers and a tri or tetra amine, or combinations of bi/tri, bi/tetra, tri/tri, tri/tetra or tetra/tetra amines carrying —NH or —NH₂ groups. A further aspect of the present disclosure includes treatment of the obtained oligomeric polyfunctional amines with hydrophobic epoxide compounds, hydrophobic glycidyl ethers or hydrophobic acrylate and (meth)acrylate compounds for the preparation of one or more hydrophobically modified oligomeric polyamine(s). The mild reaction is conducted at ambient temperature. Modifications can be carried out with all of the polyfunctional amines described above.

Another embodiment of the disclosure is the use of polyethyleneimines, polyallylamines, polyvinylamines, and polychitosans with hydrophobic epoxide compounds, hydrophobic glycidyl ethers or hydrophobic acrylate and (meth)acrylate compounds used to prepare one or more hydrophobically modified oligomeric polyfunctional amine(s).

The molecular weights were determined using the following GPC Methodology for amine testing in aqueous solutions. An HPLC unit Waters 2695 with selective gel permeation columns designated as; Guard and one 30 cm PL Aquagel-OH Mixed-M 8 µm columns. The detectors used included a Waters 410 Differential Refractometer (RI) with a Viscotek Dual Detector 270—(RALS, DP, IP, LALS). The running solvent used was deionized water with 0.2% ethylenediamine (EDA).

The polyfunctional amine crosslinker samples were diluted in DI water and filtered through 0.22 um PTFE filters into 1.5 mL vials and run through the GPC system at a flow rate of 1.0 mL/min. Each vial had a run time of 30 minutes to allow samples to be entirely flushed out before the next run. To find the Molecular weights, a set of Polyethylene Glycol (Oxide) samples were run as a calibration curve ranging from 232 to over one million Daltons. Omnisec software was used to create a method to fit the molecular weight distributions of the amine samples to the calibration curve of the standardized PEG samples.

The present disclosure involves the use of crosslinkers for the preparation of final latex polymer compositions containing at least one polyfunctional amine primarily acting as a component for ionic bonding. An example of a starting constituent as well as one resulting polyfunctional amine of the present disclosure has been designated I-x-2' schematically represented below;

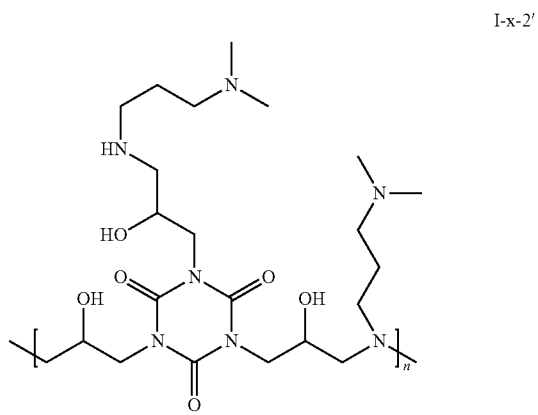

I-x-2'

Processes for Preparing Hydrophobically Modified Polyfunctional Amine Crosslinkers:

A general method for achieving the reaction leading to the oligomeric polyfunctional amine I-x-2' as represented above is as follows;

A solution of the indicated amine is charged to a 2 liter reactor and an appropriate amount of rinsing water is used to ensure that no residual remains around the sides of the reactor. This solution is then heated to 20-30° C. and thoroughly agitated, with one or multiple portions of TGIC subsequently added to the amine solution. The reaction temperature should be maintained between 20-60° C., and more preferably 35-50° C. The TGIC, which is present as a white granular substance or powder, is dissolved gradually. The reaction should be maintained at ambient temperature between 40-45° C. for another two hours. The reaction solution is discharged from the reactor (kettle) and results in final concentrations of polyamine crosslinkers preferably in the 10-80 weight % range and most preferably 20-25 weight % range. In some cases previous reactions involving the direct addition of the entire amount of TGIC resulted in polyamine crosslinkers of 20% with no water removed.

Here, equation (1) describes how the w/0 (weight percent) of the polyamine is determined:

weight % polyamine=weight of reactants/total weight (w/water)    (1)

In at least one embodiment, the crosslinkers made from the glycidyl/amine condensation chemistry of the present disclosure should include at least three amino group sites that are responsive to changes in pH and will accept or release proton(s) in response to such a change in pH and additionally, at least one —NH/—NH2 site.

The synthesis of the structure of oligomer (I-x-2'), as provided in Reaction 1, was performed using the following procedure;

(A)+(B)→(I-x-2'), where (A) is triglycidyl isocyanurate (TGIC)

(B) is a bi-functional amine (such as DMAPA), and (I-x-2') is a polyfunctional amine group with repeating units, n, of structure (I-x-2') which is derived from the I-x-b structure.

More specifically, as summarized in Table 1, a solution of 174.1 g DMAPA in 1582 g water was added to a 10 liter reactor (kettle) and stirred with a 3.5 inch pitched blade driven by a mechanical stirring motor. 98.9 g of TGIC was poured into this reactor at room temperature comprising the first TGIC portion. 8.3 g of water for rinsing was used to ensure that no residual TGIC remains. The resulting exothermic conditions of this reaction elevated the reaction temperature to 41.3° C., after ten minutes. The reaction is next cooled with an ice bath to 25-35° C., and the second portion of TGIC is added in the amount of 674.1 g. The reaction is again agitated for approximately 10 minutes and the exothermic conditions of this reaction elevate the reaction temperature to 41.3° C. The reaction is again cooled with an ice bath to 25-35° C., and 74.1 g TGIC of the third portion is then added. 46.6 g of water for rinsing was used again to ensure that no residual remains. It takes approximately 6 minutes for the TGIC powder to dissolve and the heat released from the reaction elevates the reaction by 5-10 C. The reaction is then maintained at ambient temperature between 35-45° C. for another 140 minutes. The reaction solution is finally discharged from the reactor (kettle) resulting in polyamine linker concentrations of approximately 20%. Using this procedure, the number average molecular weight (Mn) of the polyamine linker was determined to be 14,065.

TABLE 1

Summary of Method of Preparation of I-x-2' Polyamine Linker

|  | Chemical | MW | Weight (g) |
|---|---|---|---|
| Kettle | Triglycidyl isocyanurate | 297.26 | 98.9 |
|  | Triglycidyl isocyanurate | 297.26 | 74.1 |
|  | Triglycidyl isocyanurate | 297.26 | 74.1 |
|  | dimethyl aminopropylamine | 102.18 | 174.1 |
|  | Water |  | 1582.00 |

The actual reaction schema for the synthesis (preparation) of the (I-x-2') compound is provided below;

REACTION 1: Preparation of (I-x-2'), a representative TGIC/DMAPA Condensate Reaction

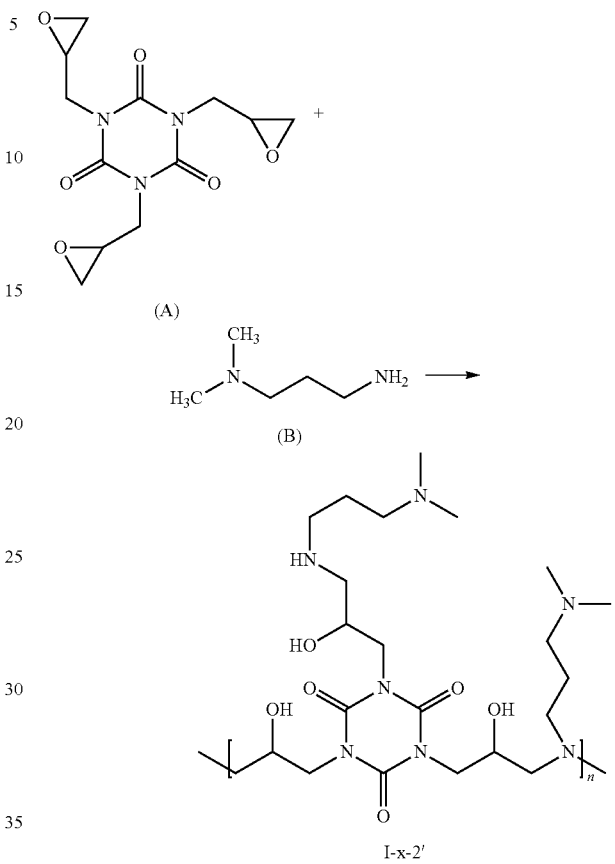

I-x-2'

Epoxide and acrylate functional groups are introduced for post hydrophobic modification providing additional sites for anchoring to the latex particles of the final latex composition. Epoxides or acrylates employed for modification provides between 5 and 100% of all available —NH or —NH2 reactive sites.

The synthesis of the structure of the oligomeric compound (I-x-2'a), includes the addition of reactive groups as shown, for example in Reaction 2, and was performed according to the following procedure;

(I-x-2')+(C)→(I-x-2'a), where (I-x-2') is a polyfunctional amine as provided in Reaction 1;

(C) is a hydrophobic epoxide (such as 1-butene oxide) and (I-x-2'a) is a hydrophobically modified polyfunctional amino group with repeating units, n, of structure (I-x-2'a).

To a 1 liter reactor, a solution of 300 g I-x-2' is charged together with 9.8 g 1-butene oxide. The solution was stirred with a mechanical stirring blade for 3 hours and ten minutes. The internal temperature was maintained between 35-40° C. The reaction was allowed to cool naturally resulting in a butane oxide modified polyfunctional amine crosslinker, (I-x-2'a). The details of the reaction are provided below;

REACTION 2:

The reactants leading to the polyfunctional polymeric/ oligomeric amine product shown above (I-x-2'a), result in the introduction of a hydrophobic moiety. Introduction of the hydrophobic moiety serves as a method of adding anchor points facilitating increased later interactions with the latex component and thereby increasing dry time and water resistance.

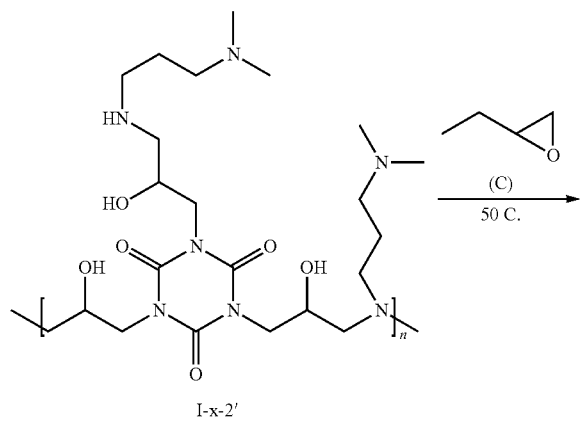

I-x-2'a

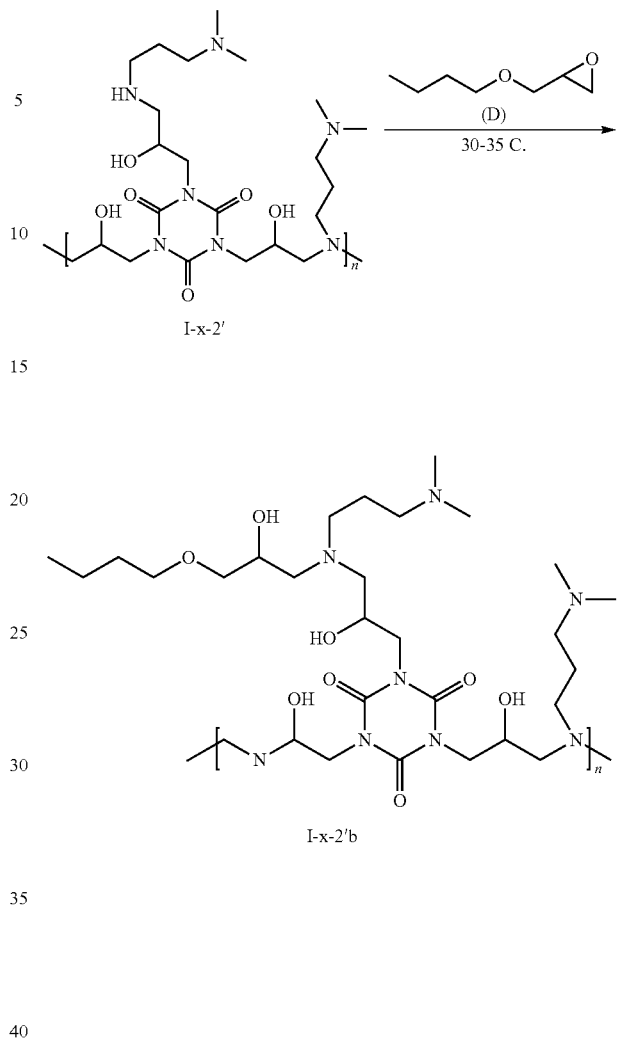

The synthesis of the structure of oligomer (I-x-2'b), which includes the addition of groups as shown in Reaction 3, was performed using the following procedure;

(I-x-2')+(D) (I-x-2'b), where (I-x-2') is a polyfunctional amine as provided in reaction 1

(D) is a hydrophobic glycidyl ether (such as butyl glycidyl ether) and (I-x-2'b) is a hydrophobically modified polyfunctional amino group with repeating units, n, of structure (I-x-2'b).

To a 1 liter reactor, a solution of 300 g I-x-2' is charged together with 10 g butyl glycidyl ether. The solution was stirred with a mechanical stirring blade for 35 minutes. The internal temperature was maintained between 30-35° C. The reaction was allowed to cool naturally resulting in a clear butyl glycidyl ether modified polyfunctional amine crosslinker, (I-x-2'b).

REACTION 3:

The reactants leading to the polyfunctional polymeric/oligomeric amine product shown above (I-x-2'b), result in the introduction of a hydrophobic moiety. Introduction of the hydrophobic moiety serves as a method of adding anchor points facilitating increased interactions with the latex component and thereby increasing dry time and water resistance.

The synthesis of the structure of oligomer (1-x-2'c), which includes the addition of groups as shown in Reaction 4, was performed using the following procedure;

(I-x-2')+(E)→(I-x-2'c), where (I-x-2') is a polyfunctional amine as provided in Reaction 1

(E) is a hydrophobic epoxide (such as cyclohexene oxide) and (I-x-2'c) is a hydrophobically modified polyfunctional amino group with repeating units, n, of structure (I-x-2'c).

To a 1 liter reactor, a solution of 300 g I-x-2' is charged together with 9 g cyclohexene oxide. The solution was stirred with a mechanical stirring blade for 3 hours. The internal temperature was maintained between 30-35° C. The reaction was allowed to cool naturally resulting in a clear cyclohexene oxide modified polyfunctional amine crosslinker, (I-x-2'c).

REACTION 4:

The reactants leading to the polyfunctional polymeric/oligomeric amine product shown above (I-x-2'c), results in the introduction of a hydrophobic moiety. Introduction of the hydrophobic moiety serves as a method of adding anchor points facilitating increased interactions with the latex component(s) and thereby increasing dry time and water resistance.

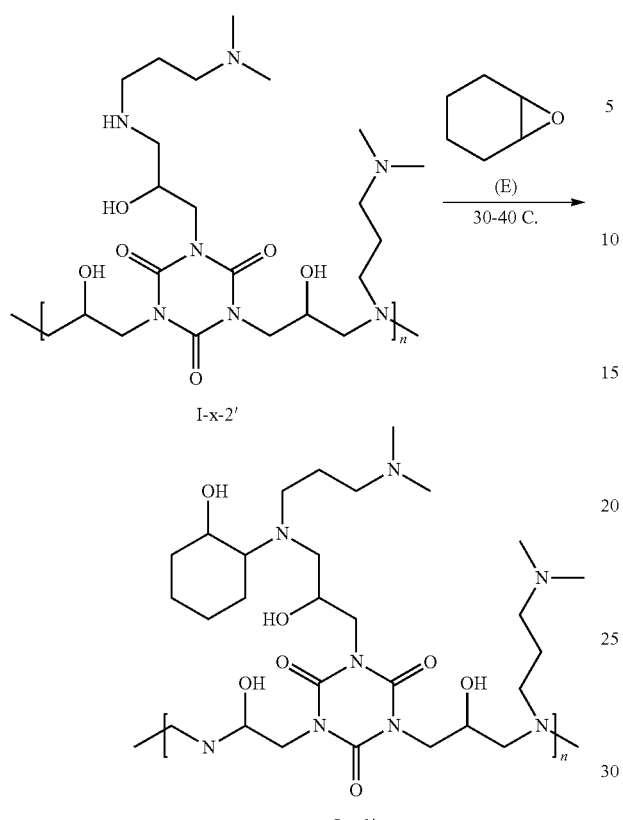

I-x-2'

I-x-2'c

The synthesis of the structure of oligomer (I-x-2'd), which includes the addition of groups as shown in Reaction 4, was performed using the following procedure;

(I-x-2')+(F)→(I-x-2'd), where (I-x-2') is a polyfunctional amine as provided in Reaction 1

(F) is a hydrophobic acrylic monomer emulsion (such as Acrylic ME) and (I-x-2'd) is a hydrophobically modified polyfunctional amino group with repeating units, n, of structure (I-x-2'd).

For this reaction, the molar ratio of (I-x-2'): Acrylic-ME is 1:0.2. The rate limiting reactant is the Acrylic-ME and in this case limits the yield of I-x-2'd.

Preparation of Acrylic Monomer Emulsion (Acrylic ME):

In a 2 L reactor, 108.0 g water, 4.6 g ADS 30%, 122.2 BA, 1453.8 MMA, and 2.8 g MAA were added and mixed with a 3 inch pitched blade at 300 rpm for 30 minutes allowing for the preparation of a homogeneous emulsion for further use in hydrophobic modification of polyfunctional amines for crosslinking of latex particles.

To a 1 liter reactor, a solution of 150 g I-x-2' and 5 g of the acrylic monomer emulsion (Acrylic ME) were charged together. The solution was stirred with a mechanical stirring blade for 15 hours. The internal temperature was maintained between 40-50° C. The reaction was allowed to cool naturally resulting in a homogeneous acrylic monomer emulsion (Acrylic ME) modified polyfunctional amine crosslinker, (I-x-2'd).

REACTION 5:

The reactants leading to the polyfunctional polymeric/oligomeric amine product shown above (I-x-2'd), result in the introduction of a hydrophobic moiety. Introduction of the hydrophobic moiety serves as a method of adding anchor points facilitating increased interactions with the latex component.

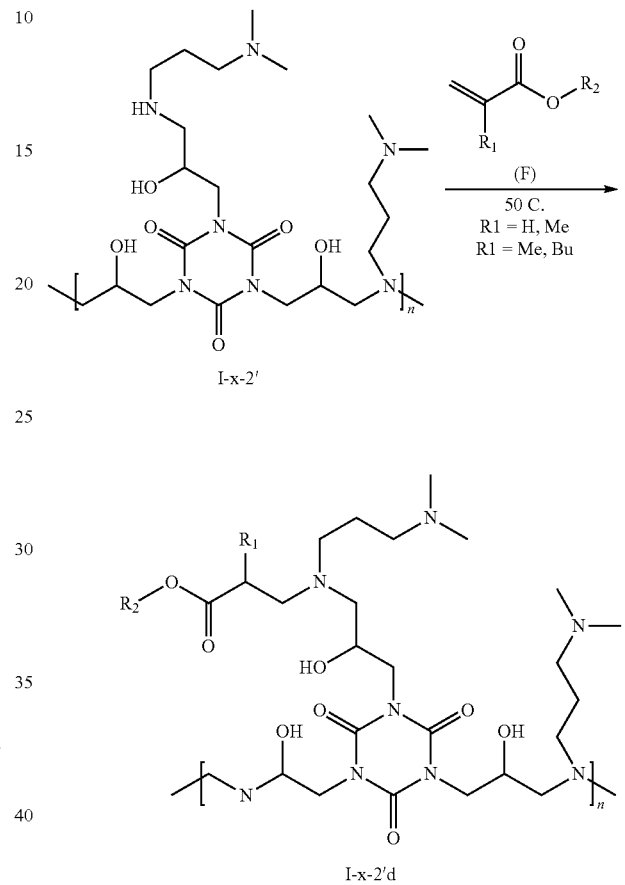

I-x-2'

I-x-2'd

These hydrophobically modified polyfunctional amine structures, shown above, are representative of one group of polyfunctional polymeric amines which possess the necessary cationic charge and molecular weight so that when placed in solution with the latex binder allows for providing a final aqueous based crosslinked polymer latex coating that forms proper films, is quick drying, and exhibits increased resistance to water wash-off.

Examples of Reaction Type II hydrophobically modified polyfunctional amine crosslinkers that are not provided by Reaction Type I products can be prepared as follows:

The synthesis of the structure (QDA-D), which includes the addition of groups as shown in Reaction 6, was performed using the following procedure;

(PEI)+(D)→(QDA-D), where (PEI) is polyethyleneimine, (D) is a hydrophobic glycidyl ether (such as butyl glycidyl ether) and (QDA-D) is a hydrophobically modified polyfunctional imine that is a quick drying agent.

REACTION 6:

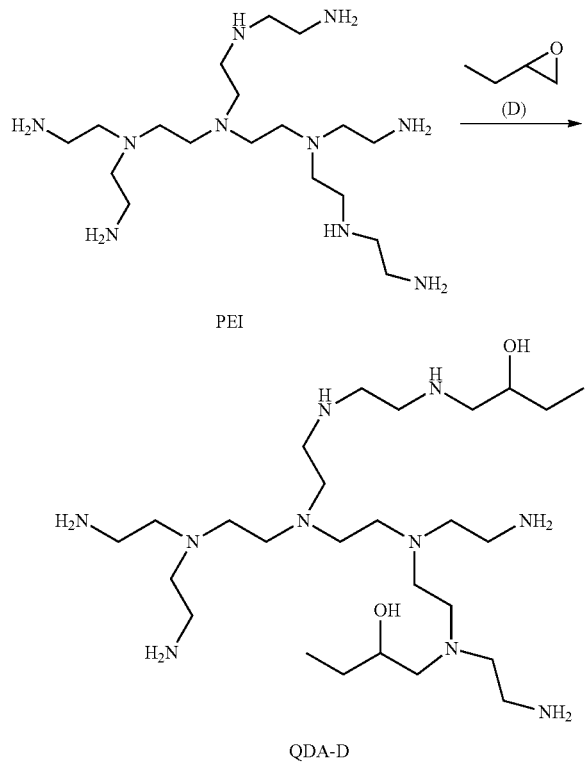

QDA-D

Preparation of Quick Drying Agent (QDA-D):

In a 250 mL bottle, 20 g water, 430 g polyethyleneimine (PEI) (50%, Mn=1200), and 10 g butyl glycidyl ether were added and mixed with a magnetic stirrer for 36 minutes at a temperature of 35-45° C. A homogeneous solution was obtained for further use in modification of polyfunctional amines for crosslinking of latex particles.

REACTION 7:

The synthesis of the structure of oligomer (QDA-F), which includes the addition of groups as shown in Reaction 7, was performed using the following reaction schema;

(PEI)+(F)→(QDA-F), where (PEI) is polyethyleneimine
- (F) is a hydrophobic acrylic monomer emulsion (such as Acrylic ME) and
- (QDA-F) is a hydrophobically modified polyfunctional imine that is a quick drying agent.

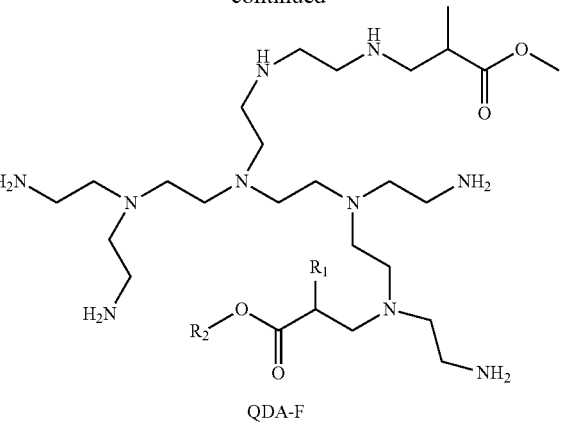

QDA-F

Method of Making Crosslinkable Latex Polymers

The latex polymer compositions of the present invention will have various properties, often depending on end-use applications. In general, the polymer component may have glass transition temperatures (Tg) of 15 to 40° C. and more preferably 20 to 30° C.

The weight average molecular weight of the latex polymer compositions may vary from about 5,000 to 5,000,000 Daltons; more preferably from 20,000 to 2,000,000 and most preferably from 40,000 to 100,000.

A waterborne polymer composition may be prepared using the latex polymer composition of the present invention along with other known additives and may also employ other emulsion polymerization methodologies.

The examples below are illustrative of the preparation of latex polymers and waterborne polymer compositions, according to one aspect of the present invention.

First a latex seed must be prepared.

A 2 liter reactor was charged with 210.9 g SDS solution (14% of the total solution), 4.6 g $NaHCO_3$, 503.3 g water, 158.0 g BA, 189.5 g MMA, 6.8 g MAA and 16.2 g APS. The solution was mechanically stirred and heated to 65 C. Radical polymerization occurred immediately to raise the temperature quickly. The exotherm was controlled using 410.1 g water which was added gradually over a period of four minutes. The seed solution was allowed to react for another 130 minutes to ensure the reaction proceeds to completion. The latex particle size obtained was determined to be 51 nm.

Latexes or other waterborne compositions contain small particle size seed polymers, those ranging from about 25 to about 700 nm, preferably from about 50 to about 500 nm and more preferably from about 75 to about 300 nm, represent one embodiment of the invention.

Next, it was necessary to prepare the latex. This procedure was performed as follows: a kettle was charged with 231.9 g water, 32.5 acrylic seed (23% solids) and 0.8 g sodium bicarbonate. Once charged, the kettle charge was heated to 80 C using a water bath. A solution of 2.1 g APS in 30 g water and the monomer emulsion, as indicated below in Table 2, was feed into the kettle over 195 minutes. To ensure no loss of reactants, 20 g of water was used to rinse the solution. While maintaining the temperature, the latex polymerization and resulting latex polymer binder was allowed to react for another 90 minutes to ensure reaction completion. Ammonium hydroxide, 16.1 g. (30%) was added to the polymerized latex emulsion after it was cooled to ambient conditions.

TABLE 2

| Constituents of Acrylic Monomer Emulsion (ME) | |
| --- | --- |
| BA | 315.9 |
| MMA | 379 |
| MAA | 13.5 |
| NaHCO3 | 0.8 |
| SDS solution (14%) | 81.92 |
| IGEPAL CA 407 | 10.2 |
| Water | 270 |

Once the latex polymerization yielding the latex binder was complete, it was possible to complete the process by producing latex paints.

The following examples are intended to illustrate, not limit, the invention:

Comparative Example 1 (White Paint)

To prepare a latex based white paint with the non-hydrophobically modified polyfunctional amine crosslinker I-x-2' (Comparative Example 1) of the present disclosure, the following procedure was employed; to a quart can containing 444.0 g of the acrylic latex polymerized based on the procedure described above for preparing the dry latex, 11.1 g of I-x-2' untreated crosslinker solution was added and the mixture was stirred for 5 minutes using a high sheer mixing blade at moderate speed. Next 8.0 g dispersant was added along with 5.0 g defoamer, 2.5 g surfactant, and 0.2 g biocide while stirring with a high sheer mixing blade at a moderate speed, normally not greater than 100 rpm, for another 5 minutes. Next a rheology agent and/or thickener was mixed with 19.6 g of water and added to the stirring mixture and stirred at high speed for another 5 minutes. To this, 0.8 g ammonia was added bringing the pH to 9.6. Then pigments, extenders, and calcium carbonate were added carefully while stirring at high speed for 15 minutes. After completion of the mixing and accompanying grinding, 30.0 g of solvent was added slowly and at a reduced stirring speed to which 5.6 g coalescent was added to the mixture with continued stirring. Next, 20 g of the co-solvent coalescent was added and stirred into the mixture. The total contents of the solution were then continuously stirred for another 5 minutes until complete.

Examples 1-5 (White Paint)

The same procedure as provided for Comparative Example 1 is used for Examples 1-5 (as described in Table 3 below), with the exception being the type and amount of crosslinker selected. The dry weight ratio of crosslinker to dry latex polymer for each of Examples 1-5 is 1:100. Comparative Example 2 is provided as the yellow paint counterpart to that of Comparative Example 1.

Table 3 below summarizes the polyfunctional amine crosslinker content using the described procedures and resulting latex paint solutions.

TABLE 3

Polyfunctional Amine Crosslinker Content of Latex Paints with and without Hydrophobic Modification

| Latex Components (g) | Example 1 | Example 2 | Example 3 | Example 4 | Example 5 | Example 6 | Comp. Ex. 1 | Comp. Ex. 2 |
| --- | --- | --- | --- | --- | --- | --- | --- | --- |
| Crosslinker I-x-2' | — | — | — | — | — | — | 11.1 g | 11.0 g |
| Crosslinker I-x-2'a | 9.7 g | — | — | — | — | 9.6 g | — | — |
| Crosslinker I-x-2'b | — | — | — | 10.1 g | — | — | — | — |
| Crosslinker I-x-2'c | — | — | — | — | 10.6 g | — | — | — |
| Crosslinker I-x-2'd | — | 10.3 g | — | — | — | — | — | — |
| QDA | — | — | 7.1 g | — | — | — | — | — |

Comparative Example 2 (Yellow Paint)

To prepare a latex based yellow paint with the non-hydrophobically modified polyfunctional amine crosslinker I-x-2' (Comparative Example 2), the following procedure was employed; to a quart can containing 439.0 g of the acrylic latex polymerized based on the procedure above for preparing the dry latex, 11.0 g of I-x-2' untreated crosslinker solution was added to providing a mixture that was stirred for over 2 minutes using a high sheer mixing blade at moderate speed. Then 8.0 g dispersant, 3.0 g surfactant, 6.0 g defoamer, and 0.2 g biocide were added while stirring with a high sheer mixing blade at a moderate speed, normally not greater than 100 rpm, for another 5 minutes. 0.4 g rheology agent or thickener was then mixed with 28.3 g water and added to the stirring mixture and stirred at higher speeds (normally not greater than 1000 rpm) for another 5 minutes. The pH of the mixture was checked and adjusted to 9.8 with ammonium hydroxide as needed. 19.0 g organic pigment, 1.0 g inorganic pigment, 25.0 g titanium oxide, and 189.6 g of an inorganic extender was then added carefully while stirring at the same higher speed for 15 minutes. After grinding was completed, 33.0 g of solvent was added slowly at a reduced stirring speed (300-500 rpm). 3.0 g coalescent was added to the mixture while stirring continuously. Next, 20.0 g of co-solvent was added and stirred into the mixture. The total content of the solution was then continuously stirred for another 5 minutes until complete.

Example 6 (Yellow Paint)

Example 6 was a yellow paint containing the hydrophobically modified crosslinker I-x-2'a. This paint was achieved with the addition of 9.6 g of Example 1 (containing the polyfunctional amine crosslinker I-x-2'a) into 439.0 g latex by stirring the mixture for two minutes. Next, 8.0 g dispersant, 3.0 g surfactant, 6.0 g defoamer, and 0.2 g biocide were added while the mixture was being stirred with a high sheer mixing blade at moderate speed (normally less than 100 rpm) for 5 minutes. In addition, 0.4 g thickener was mixed with 28.3 g water and added to the stirring mixture. Stirring at higher speeds (normally less than 1000 rpm) continued for another 5 minutes. The pH of the mixture was checked and adjusted to 9.8 with ammonium hydroxide as needed. Next 19.0 g organic pigment, 1.0 g inorganic pigment, 25.0 g titanium oxide, and 189.6 g inorganic extender were added while stirring at the same higher speed for 15 minutes. After grinding was completed, 33.0 g of solvent was added slowly at a reduced stirring speed (300-500 rpm). 3.0 g coalescent was added to the mixture while stirring continuously. Next 20.0 g of co-solvent was added and stirred into the mixture. The total content of the solution was then continuously stirred for another 5 minutes until complete.

Test Methods

To determine the effectiveness of the polyfunctional amine crosslinkers, a water wash-off test was performed to compare 30 minutes dry time for both Example 1 and Comparative Example 1 according to the procedures detailed in ASTM D711-10.

This is the procedure for paint film preparation and dry time test:

A sample of paint is drawn to 15 mil wet film thickness onto to a clean black scrub test panel and allowed to dry horizontally in a conditioned room at 23° C.±2° C. and 75% relative humidity under a constant 2 mph air flow. Standard method ASTM D711-10 was used to judge the no tire pick up dry time.

Water Immersion Testing

A 15-mil wet draw down is performed on scrub panels. The panel is allowed to dry for 25 minutes under the following conditions of 1) 2±0.2 mph wind speed; 2) 50%±5% relative humidity; 3) 75° F.±2° F. When the paint film is ready, the panel carrying the paint film is immersed into water in such a way that half of the paint film is merged into water and the remaining half is exposed to the air. The water temperature in this case should be 72° F.±2° F. Thirty (30) minutes later, the panel should be removed and the percentage of blistering area recorded. Results of the water immersion test are provided below in Tables 4 and Table 5 for white and yellow latexes respectively.

TABLE 4

Results of Water Immersion Testing for White Latex Compositions Containing Different Amounts of Hydrophobically Modified Polyfunctional Amine Crosslinkers

| Sample | Dry Time | Water Blistering % |
| --- | --- | --- |
| Comparative Example 1 | 12.0 | 43 |
| Example 1 | 9.0 | 60 |
| Example 2 | 12.75 | 0 |
| Example 3 | 9.5 | 20 |
| Example 4 | 9.1 | 40 |
| Example 5 | 11.0 | 18 |

TABLE 5

Results of Water Immersion Testing for Yellow Latex Compositions Containing Different Amounts of Hydrophobically Modified Polyfunctional Amine Crosslinkers

| Sample | Dry Time | Water Blistering % |
| --- | --- | --- |
| Comparative Example 2 | 11.5 | 65 |
| Example 6 | 7.25 | 10 |

Water-Wash Off

The water wash-off procedure generally follows the ASTM D7377-08 procedure but is modified by using section 4.6.2 of ASTM D711-10 for controlled air flow. Paint viscosity is determined by measuring Krebs Units (KU) using a paddle type viscometer. Viscosities of 80 to 90 KU are considered suitable for testing.

Drawdown Samples are Prepared Via the Procedure Provided Herein:

A sample of paint is drawn to 15 mil wet film thickness onto to a clean black scrub test panel and allowed to dry horizontally for 15 to 60 minutes in a conditioned room at 23° C.±2° C. and 50 to 55% relative humidity under a constant 2 mph air flow. When the drying time is complete, the samples are placed under a stream of 25° C. tap water flowing at a rate of 1.5 gal/min and allowed to remain there for 5 minutes, during which the time of film break through is recorded. After completion of the test, the samples are then removed from the flowing water and observed to note the percentage of wash off.

Surfactants

In the present disclosure, a combination of an anionic surfactant and a non-ionic surfactant is used. The type of anionic surfactants provided are not limited to: sodium dodecyl sulfate (SDS), ammonium dodecylsulfate (ADS), disodium salt of ethoxylated lauryl sulfosuccinate and sodium benzyl dodecyl sulfate. The nonionic surfactants of the present disclosure include but are not limited to IGEPAL CA-407® (available from Rhodia Inc.), Triton™ X-100 (available from Dow, Inc.), Triton™ X-405 (available from Dow, Inc.) and E-Sperse® 703 (available from Ethox, Inc.).

The polymers and waterborne polymer compositions of the present disclosure invention are useful in a variety of paint and coating formulations such as; architectural coatings, metal coatings, wood coatings, plastic coatings, textile coatings, cementitious coatings, paper coatings, inks, and adhesives. Examples of such coating formulations adapted for particular uses include, but are not limited to, corrosion inhibitors, concrete coatings, maintenance coatings, latex paints, industrial coatings, automotive coatings, textile backcoatings, surface printing inks and laminating inks. Accordingly, the present invention relates to such coating formulations containing a waterborne polymer composition of the invention, preferably a water-based latex. The polymers and waterborne polymer compositions of the invention may be incorporated in those coating formulations in the same manner as known polymer latexes and used with the conventional components and or additives of such compositions. The coating formulations may be clear or pigmented. With their crosslinking ability, adhesion properties, and resistance properties, the water-based latexes of the invention impart new and/or improved properties to the various coating formulations.

Upon formulation, a coating/paint formulation containing a latex polymer or waterborne polymer composition of the invention may then be applied to a variety of surfaces, substrates, or articles, e.g., paper, plastic, steel, aluminum, wood, gypsum board, concrete, brick, masonry, or galvanized sheeting (either primed or unprimed). The type of surface, substrate, or article to be coated generally determines the type of coating formulation used. The coating formulation may be applied using means known in the art. For example, a coating formulation may be applied by spraying or by coating a substrate. In general, the coating may be dried by heating but preferably is allowed to air dry. Advantageously, a coating employing a polymer of the invention may be thermally or ambiently cured. As a further aspect, the present invention relates to a shaped or formed article which has been coated with coating formulations of the present invention.

A waterborne polymer composition according to the invention may further comprise water, along with a solvent, a pigment (organic or inorganic) and/or other additives and fillers known in the art, and enumerated below. When a solvent is used, water-miscible solvents are preferred. A latex paint composition of the present disclosure may comprise a waterborne polymer composition of the present invention, a pigment, and one or more additives or fillers used in latex paints.

Additives or fillers used in formulating coatings include, but are not limited to, leveling, rheology, and flow control agents such as silicones, fluorocarbons, urethanes, or cellulosics; extenders; curing agents such as multifunctional isocyanates, multifunctional carbonates, multifunctional epoxides, or multifunctional acrylates; reactive coalescing aids such as those described in U.S. Pat. No. 5,349,026; flatting agents; pigment wetting and dispersing agents and surfactants; ultraviolet (UV) absorbers; UV light stabilizers; tinting pigments; extenders; defoaming and antifoaming agents; anti-settling, anti-sag and bodying agents; anti-skinning agents; anti-flooding and anti-floating agents; fungicides and mildewcides; corrosion inhibitors; thickening agents; plasticizers; reactive plasticizers; drying agents; catalysts; crosslinking agents; or coalescing agents. Specific examples of such additives can be found in *Raw Materials Index*, published by the National Paint & Coatings Association, 1500 Rhode Island Avenue, NW, Washington, D.C. 20005.

A polymer or waterborne polymer composition of the present invention can be utilized alone or in conjunction with other conventional waterborne polymers. Such polymers include, but are not limited to, water dispersible polymers such as consisting of polyesters, polyester-amides, cellulose esters, alkyds, polyurethanes, epoxy resins, polyamides, and acrylics.

The present disclosure and associated invention has been described in detail with particular reference to embodiments thereof, but it will be understood that variations and modifications can be effected within the spirit and scope of the invention.

I claim:

1. A polyfunctional amine comprising recurring units derived from the reaction of one bi- or tri-glycidyl moiety and a single, di-, or tri-functional amino monomer(s), or combination of, mono/tri, mono/tetra, bi/bi, bi/tri, bi/tetra, tri/tri, tri/tetra, and tetra/tetra functional amino monomers resulting in one or more polyfunctional amines

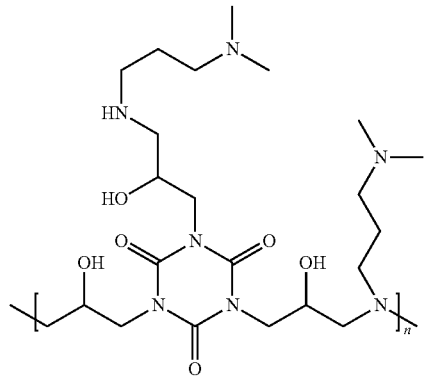

I-x-2-b' wherein I-x-2-b' is a hydrophobic crosslinking agent and comprises at least three pH responsive amino group sites configured to accept or release proton(s) in response to a change in pH, and comprises at least one NH and/or one —NH$_2$ site providing reactive sites for hydrophobic compounds that introduce at least one hydrophobic moiety into hydrophobic modifications of I-x-b-2' structures represented by formulae I-x-b-2' a, I-x-b-2'b, I-x-b-2'c and I-x-b-2'd:

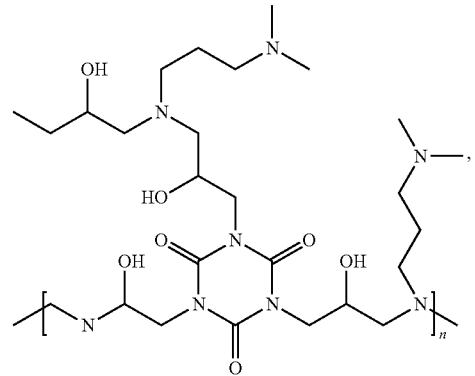

I-x-b-2'a

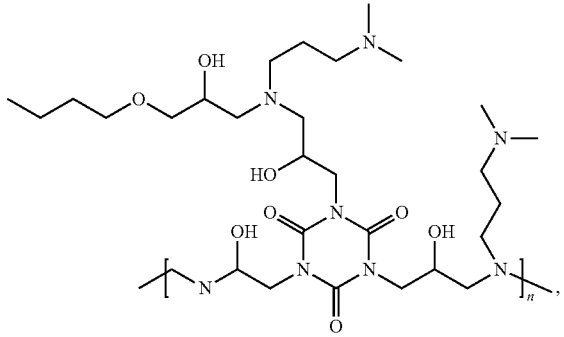

I-x-b-2'b

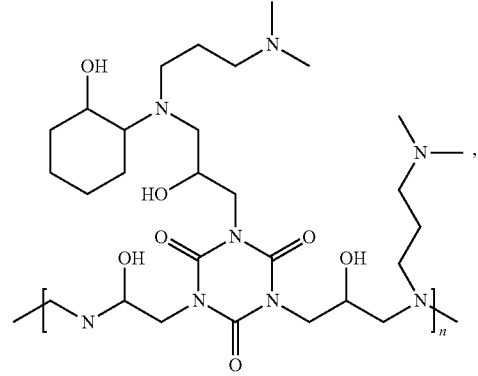

I-x-b-2'c

-continued

I-x-b-2'd

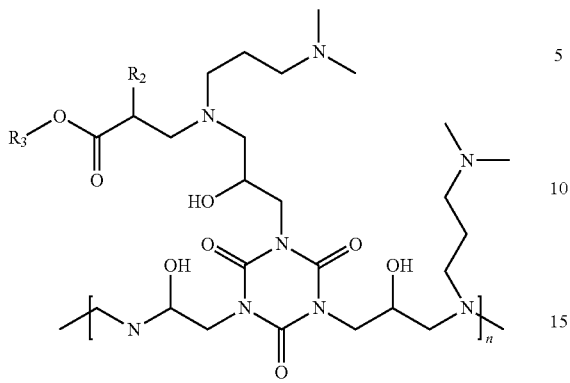

wherein said structures of formulae I-x-b-2'a, I-x-b-2'b, I-x-b-2'c and I-x-b-2'd have at least one hydrophobic moiety introduced into said structures from the group consisting of: hydrophobic epoxides, hydrophobic glycidyl ethers and hydrophobic (meth)acrylates.

2. The polyfunctional amine of claim 1, wherein said hydrophobic moiety is provided by post modification reactions with said epoxides, glycidyl ethers and (meth)acyrlates at ambient temperature and pressure.

3. A latex formulation comprising the polyfunctional amine of claim 1.

4. The latex formulation of claim 3, wherein said hydrophobic moiety is provided by carrying out post modification reactions with said epoxides, glycidyl ethers and (meth)acrylates at ambient temperature and pressure.

* * * * *